(12) United States Patent
Roh et al.

(10) Patent No.: US 11,872,013 B2
(45) Date of Patent: Jan. 16, 2024

(54) SHOE-TYPE DEVICE AND METHOD OF CONTROLLING THE SAME

(71) Applicant: Samsung Electronics Co., Ltd., Suwon-si (KR)

(72) Inventors: Changhyun Roh, Suwon-si (KR); Segon Roh, Suwon-si (KR); Youngbo Shim, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 547 days.

(21) Appl. No.: 17/004,193

(22) Filed: Aug. 27, 2020

(65) Prior Publication Data

US 2021/0186331 A1 Jun. 24, 2021

(30) Foreign Application Priority Data

Dec. 24, 2019 (KR) ........................ 10-2019-0173847

(51) Int. Cl.
*A61B 5/00* (2006.01)
*A43B 17/00* (2006.01)
*A61B 5/103* (2006.01)
*A43B 3/34* (2022.01)

(52) U.S. Cl.
CPC .............. *A61B 5/0051* (2013.01); *A43B 3/34* (2022.01); *A43B 17/00* (2013.01); *A61B 5/1038* (2013.01); *A61B 5/6807* (2013.01); *A61B 2562/0247* (2013.01)

(58) Field of Classification Search
CPC ... A61B 5/0051; A61B 5/1038; A61B 5/6807; A61B 2562/0247; A61B 5/1116; A61B 5/112; A61B 5/7455; A61B 5/1036; A61B 5/486; A61B 5/6802; A43B 3/34; A43B 17/00; A43B 3/44; A61H 2201/165
See application file for complete search history.

(56) References Cited

U.S. PATENT DOCUMENTS

| 5,357,696 | A | 10/1994 | Gray et al. |
| 8,844,166 | B2 | 9/2014 | Jazdanian |
| 9,456,675 | B1 | 10/2016 | Haas |
| 10,595,749 | B1* | 3/2020 | Javitt ................ A61B 5/7455 |
| 2004/0173220 | A1* | 9/2004 | Harry ................ A61N 1/32 |
| | | | 128/892 |

(Continued)

FOREIGN PATENT DOCUMENTS

KR 10-0795830 B1 1/2008
WO WO-2010/079207 A1 7/2010

(Continued)

OTHER PUBLICATIONS

Extended European Search Report dated Mar. 30, 2021, for the corresponding EP Application No. 20204549.8.

*Primary Examiner* — Patrick Fernandes
(74) *Attorney, Agent, or Firm* — Harness, Dickey & Pierce, P.L.C.

(57) ABSTRACT

A shoe-type device and a method of controlling the shoe-type device are disclosed. The shoe-type device includes a vibrator configured to generate a vibration, a pressure sensor disposed under the vibrator and configured to measure a pressure, and a controller configured to control an intensity of the vibration to be generated by the vibrator based on the measured pressure.

28 Claims, 12 Drawing Sheets

(56) References Cited

U.S. PATENT DOCUMENTS

| | | | |
|---|---|---|---|
| 2007/0203435 A1* | 8/2007 | Novak | A43B 17/00 |
| | | | 601/46 |
| 2011/0251520 A1 | 10/2011 | Shieh et al. | |
| 2012/0154153 A1* | 6/2012 | Agrawal | A61B 5/0051 |
| | | | 36/136 |
| 2016/0193102 A1 | 7/2016 | Roh et al. | |
| 2017/0112712 A1 | 4/2017 | Chawan et al. | |
| 2020/0187830 A1 | 6/2020 | Roh | |

FOREIGN PATENT DOCUMENTS

| WO | WO-2018/037146 A1 | 3/2018 |
|---|---|---|
| WO | WO-2019/205241 A1 | 10/2019 |

\* cited by examiner

SHOE-TYPE DEVICE AND METHOD OF CONTROLLING THE SAME

CROSS-REFERENCE TO RELATED APPLICATION

This application claims under 35 U.S.C. § 119 to Korean Patent Application No. 10-2019-0173847 filed on Dec. 24, 2019, in the Korean Intellectual Property Office, the entire contents of which are incorporated herein by reference in their entirety.

BACKGROUND

1. Field

At least one example embodiment relates to a shoe-type device and a technology for controlling the shoe-type device.

2. Description of the Related Art

A user wears shoes in daily life. The shoes have a basic function of protecting the feet of the user comfortably and safely. Recently, shoes having a special function in addition to such a basic function have been developed and released. For example, there are various types of shoes, for example, shoes that automatically provide an electric stimulus to soles of the feet of a user when the user walks with the shoes on, and shoes that detect a gait pattern of a user through a sensor. As such, shoes have evolved into a wearable device having various advanced functions.

SUMMARY

Some example embodiments relate to a shoe-type device.

In some example embodiments, the shoe-type device includes a vibrator configured to generate a vibration; a pressure sensor under the vibrator, the pressure sensor configured to measure a measured pressure; and a controller configured to control an intensity of the vibration generated by the vibrator based on the measured pressure.

In some example embodiments, at least a portion of the pressure sensor overlaps the vibrator in a direction vertical to a bottom surface of the shoe-type device.

In some example embodiments, the pressure sensor completely overlaps an area of the vibrator in the direction vertical to the bottom surface of the shoe-type device.

In some example embodiments, the vibrator completely overlaps an area of the pressure sensor in the direction vertical to the bottom surface of the shoe-type device.

In some example embodiments, the pressure sensor and the vibrator form a vertical layer structure and have a same center position in a first direction.

In some example embodiments, the pressure sensor is attached to an underside of the vibrator.

In some example embodiments, the vibrator and the pressure sensor are integrally formed.

In some example embodiments, the controller is configured to set a vibration frequency of a vibration generated by the vibrator different from a sensing frequency of the pressure sensor.

In some example embodiments, the controller is configured to control the vibrator such that the intensity of the vibration decreases, in response to a decrease in the measured pressure.

In some example embodiments, the controller is configured to control the vibrator such that the intensity of the vibration increases, in response to an increase in the measured pressure.

In some example embodiments, the controller is configured to, set the intensity of the vibration as a first intensity, in response to the measured pressure being a first pressure, and set the intensity of the vibration as a second intensity greater than the first intensity, in response to the measured pressure being a second pressure greater than the first pressure.

In some example embodiments, the controller is configured to determine the intensity of the vibration based on the measured pressure and pressure-vibration intensity conversion information.

In some example embodiments, the vibrator is configured to generate the vibration such that the intensity of the vibration is less than a sensory threshold of a user wearing the shoe-type device.

In some example embodiments, the vibrator includes a first vibrator and a second vibrator, the first vibrator configured to generate a vibration at a position corresponding to a forefoot of a foot of a user, and the second vibrator configured to generate a vibration at a position corresponding to a rearfoot of the foot of the user, and the pressure sensor includes a first pressure sensor and a second pressure sensor, the first pressure sensor being under the first vibrator; and the second pressure sensor being under the second vibrator.

In some example embodiments, the controller is configured to, determine an intensity of a first vibration generated by the first vibrator based on a pressure measured by the first pressure sensor; and determine an intensity of a second vibration generated by the second vibrator based on a pressure measured by the second pressure sensor.

In some example embodiments, the controller is configured to control the first vibrator and the second vibrator such that the intensity of the first vibration and the intensity of the second vibration differ from each other.

Some example embodiments relate to a method of controlling a shoe-type device, the shoe-type device including a vibrator, a pressure sensor under the vibrator, and a controller.

In some example embodiments, the method includes measuring, via the pressure sensor, a measured pressure; and controlling, by the controller, an intensity of a vibration generated by the vibrator based on the measured pressure.

In some example embodiments, at least a portion of the pressure sensor overlaps the vibrator in a direction vertical to a bottom surface of the shoe-type device.

In some example embodiments, the controlling includes controlling the vibrator such that the intensity of the vibration decreases, in response a decrease in the measured pressure; and controlling the vibrator such that the intensity of the vibration increases, in response to an increase in the measured pressure.

In some example embodiments, the vibrator includes a first vibrator and a second vibrator, the first vibrator configured to generate a vibration at a position corresponding to a forefoot of a foot of a user, and the second vibrator configured to generate a vibration at a position corresponding to a rearfoot of the foot of the user, and the pressure sensor includes a first pressure sensor and a second pressure sensor, the first pressure sensor being under the first vibrator, and the second pressure sensor being under the second vibrator. The controlling may include determining an intensity of a first vibration generated by the first vibrator based on a pressure measured by the first pressure sensor; and determining an intensity of a second vibration generated by the second vibrator based on a pressure measured by the second pressure sensor.

Some example embodiments relate to an insole of a shoe-type device.

In some example embodiments, the insole includes an insole body insertable in the shoe-type device; a vibrator installed in the insole body, the vibrator configured to generate a vibration; and a pressure sensor under the vibrator in the insole body, the pressure sensor configured to measure a measured pressure.

In some example embodiments, at least a portion of the pressure sensor overlaps the vibrator in a direction vertical to a bottom surface of the insole.

In some example embodiments, the vibrator includes a first vibrator and a second vibrator, the first vibrator configured to generate a vibration at a position corresponding to a forefoot of a foot of a user, and the second vibrator configured to generate a vibration at a position corresponding to a rearfoot of the foot of the user, and the pressure sensor includes a first pressure sensor and a second pressure sensor, the first pressure sensor being under the first vibrator, and the second pressure sensor being under the second vibrator.

In some example embodiments, an intensity of the vibration generated by the vibrator is based on the measured pressure.

In some example embodiments, the intensity of the vibration is based on the measured pressure such that the intensity of the vibration varies directly with the measured pressure.

In some example embodiments, the insole further includes a connector configured to connect the vibrator and the pressure sensor to a controller.

In some example embodiments, the connector is configured to at least partially protrude from the insole body downwards towards an outsole of the shoe-type device to contact a terminal of the controller.

In some example embodiments, the insole further includes the controller connected to the vibrator and the pressure sensor via the connector, the controller configured to control an intensity of the vibration generated by the vibrator based on the measured pressure.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
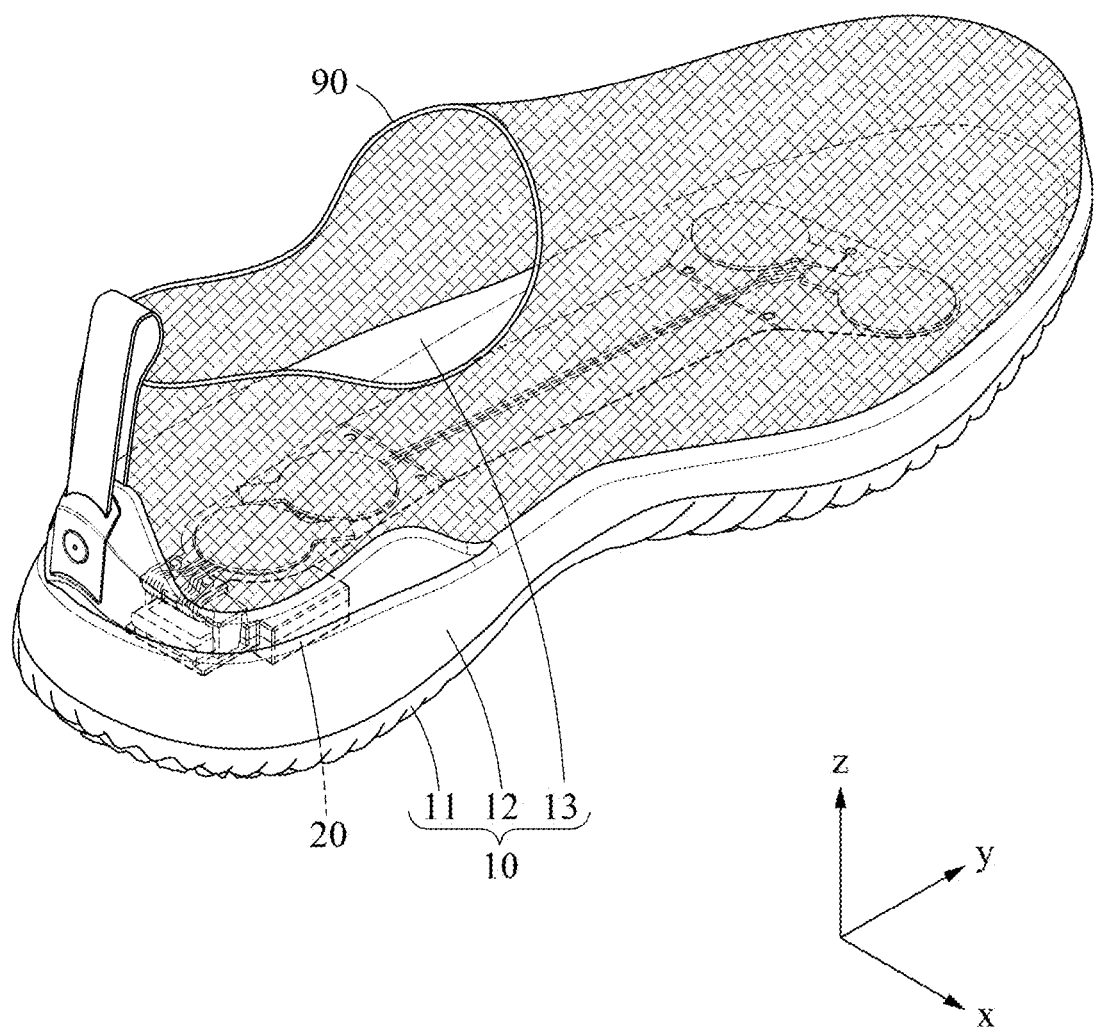
FIG. 1 is a perspective view of an example of a shoe-type device according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms, including technical and scientific terms, used herein have the same meaning as commonly understood by one of ordinary skill in the art to which the disclosure of this application pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Various example embodiments will now be described more fully with reference to the accompanying drawings in which some example embodiments are shown. In the drawings, the thicknesses of layers and regions are exaggerated for clarity.

A shoe-type device to be described hereinafter may include an electronic device configured to generate a vibration. For example, the shoe-type device may include a vibrator that may generate a physical vibration based on a control signal. The vibrator may be embedded in the shoe-type device, or an insole, and provide a user wearing the shoe-type device with a stimulus of a magnitude less than a sensory threshold of the user. The sensory threshold refers to a minimum magnitude of a stimulus that activates cells of the plantar sole of the user. The vibrator may generate the vibration having an intensity less than or equal to a threshold of a tactile sensation felt by a plantar sole of a foot of the user, thereby triggering stochastic resonance. The stochastic resonance refers to a phenomenon where a level of sensitivity to an observation target signal is improved when, to a measuring device or a sensory organ having a fixed sensory threshold, white noise of a magnitude less than or equal to the sensory threshold is applied. For example, the vibration generated by the vibrator of the shoe-type device may amplify a tactile signal to be transferred to the plantar sole of the foot of the user through the stochastic resonance, and thus the user may feel more sensitively a sensation on the plantar sole of the foot of the user. Thus, the shoe-type device may help those who may not normally feel a sensation due to a reduced sensory ability of their feet.

Hereinafter, example embodiments will be described in detail with reference to the accompanying drawings, and like reference numerals in the drawings refer to like elements throughout.

Figure 2:
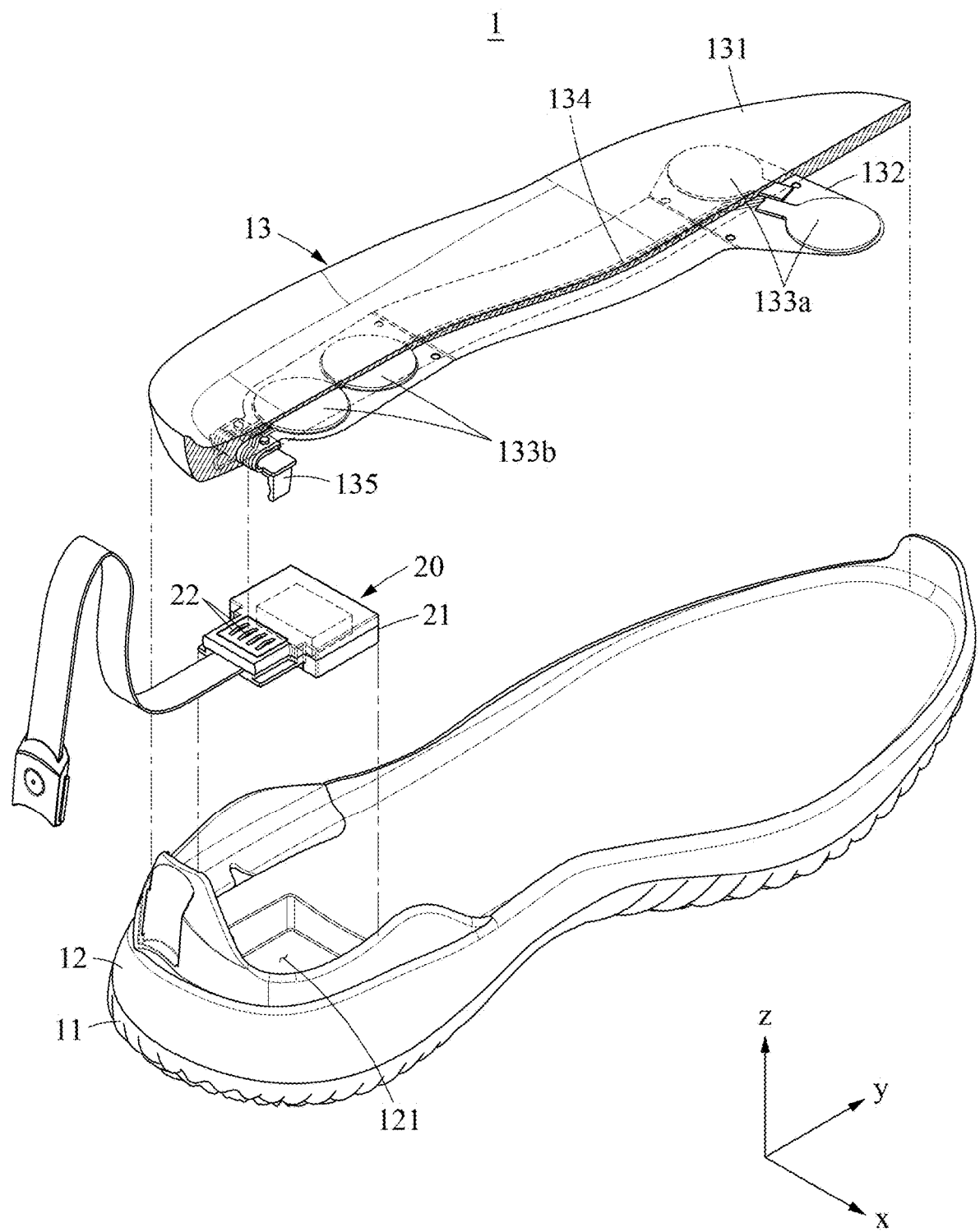
FIG. 2 is an exploded perspective view of an example of a shoe-type device according to at least one example embodiment.
Figure 3:
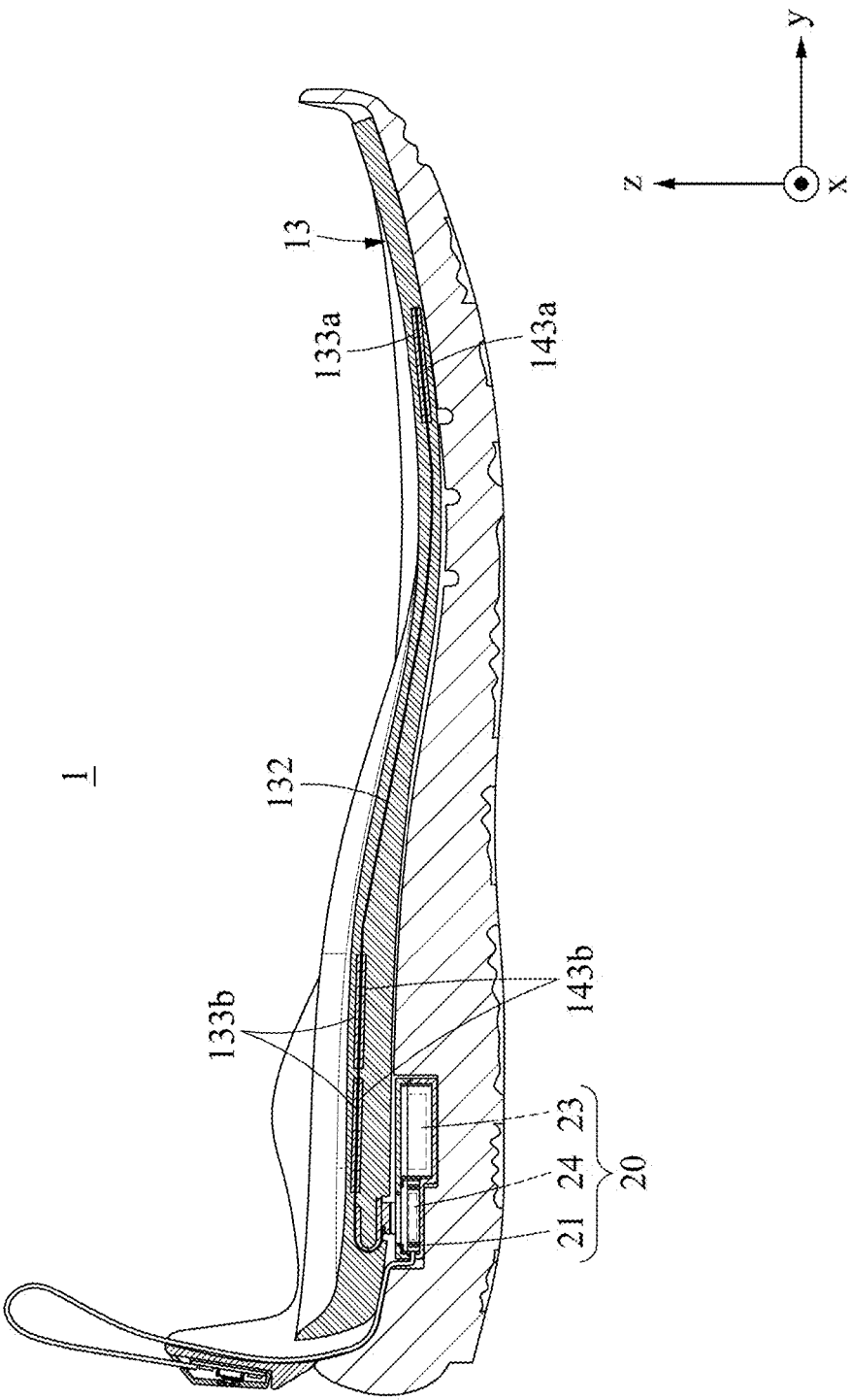
FIG. 3 is a cross-sectional view of an example of a shoe-type device according to at least one example embodiment.

FIG. 1 is a perspective view of an example of a shoe-type device according to at least one example embodiment. FIG. 2 is an exploded perspective view of an example of a shoe-type device with an insole body being separately shown according to at least one example embodiment. FIG. 3 is a cross-sectional view of an example of a shoe-type device according to at least one example embodiment.

Referring to FIGS. 1 through 3, a shoe-type device 1 includes a sole 10, a control device 20, and an upper 90. The sole 10 includes an outsole 11, a midsole 12, and an insole 13. Hereinafter, a longitudinal direction of the shoe-type device 1 will indicate a y-axis direction, a width direction of the shoe-type device 1 will indicate an x-axis direction, and a height direction of the shoe-type device 1 will indicate a z-axis direction. The shoe-type device 1 is provided in a form of a shoe, for example. However, the form of the shoe-type device 1 is not limited to the foregoing example. For example, the shoe-type device 1 may be provided in a form of a sock, and be applied to an exercise assist robot.

The outsole 11 forms at least a portion of a bottom part of the shoe-type device 1. For example, the outsole 11 includes a bottom surface that is brought into contact with the ground when a user wears the shoe-type device 1. Although the outsole 11 and the midsole 12 are illustrated as being separate, the outsole 11 and the midsole 12 may be provided in an integral form. The midsole 12 forms at least a portion of an outer lower shape of the shoe-type device 1. The insole 13 is provided inside the upper 90 and disposed on the midsole 12. The insole 13 includes a surface that is brought into contact with a plantar sole of a foot of the user when the user wears the shoe-type device 1, and is detachable from the midsole 12.

The insole 13 includes an insole body 131, a support layer 132, an electronic device, a connecting line 134, and a connector 135. The insole body 131 is disposed on a top surface of the midsole 12, and may be provided in various shapes. The support layer 132 is provided on an inner side of the insole body 131 and may support the electronic device and the connecting line 134. The connecting line 134 may electrically connect the electronic device and the control device 20. The connector 135 may electrically connect each electronic device to the control device 20.

The electronic device is disposed on a top surface of the support layer 132. The electronic device and the support layer 132 are disposed as a whole in the insole body 131. However, examples are not limited to the illustrated example, and a portion of the electronic device may be exposed to an outside of the insole body 131.

The electronic device includes at least one vibrator, for example, a vibrator 133a and a vibrator 133b as illustrated, and at least one pressure sensor, for example, a pressure sensor 143a and a pressure sensor 143b as illustrated. The vibrator may include, for example, a piezoelectric motor (or simply piezo motor) or an eccentric vibration motor. The vibrator may generate a physical vibration having an intensity less than or equal to a set maximum vibration intensity. The intensity may change irregularly as in noise. The pressure sensor, which is a sensor configured to measure a pressure applied thereto, may sense a foot pressure to be transferred from the plantar sole of the foot of the user when the user wears the shoe-type device 1. The pressure sensor may be a piezoelectric pressure sensor (or simply piezo pressure sensor) or a force sensitive resistor (FSR) pressure sensor, and be embodied in a form of a film.

The pressure sensor may not be disposed separately from the vibrator, but be disposed under where the vibrator is disposed. For example, as illustrated, the pressure sensor, for example, the pressure sensors 143a and 143b, may overlap the vibrator, for example, the vibrators 133a and 133b, in at least a portion in a direction vertical to a bottom surface of the shoe-type device 1. As such, the pressure sensor and the vibrator may form a vertical layer structure.

According to an example, the electronic device may further include another sensor, for example, an inertial sensor such as an acceleration sensor and a gyro sensor. The inertial sensor may be used to measure a movement of the shoe-type device 1 or a movement of the user wearing the shoe-type device 1.

The control device 20 may be electrically connected to the electronic device, and thus receive sensor data from the pressure sensor or another sensor included in the electronic device. In addition, the control device 20 may transmit, to the vibrator, a control signal for controlling an operation of the vibrator.

The control device 20 includes a case 21, a connecting portion 22, a battery 23, and a controller 24. The case 21 is provided in a form corresponding to a receiving groove 121 formed in the midsole 12. The connecting portion 22 includes a terminal to be electrically connected to the connecting line 134, and is disposed on an upper side of the case 21. The battery 23 may provide power that is needed for the shoe-type device 1 to operate. For example, the battery 23 may provide power to the electronic device and the controller 24, and include a rechargeable battery.

The controller 24 includes at least one processor, and may control an operation of the shoe-type device 1.

The controller 24 may generate a control signal to control an operation of the electronic device. For example, the controller 24 may generate one or more control signals for controlling respective ones of the vibrators based on a pressure measured by the pressure sensor, and one or more control signals for adjusting the number of vibrations to be generated by the respective ones of the vibrators and/or a maximum vibration intensity of the respective ones of the vibrators.

For example, the controller 24 associated with the shoe-type device 1 may include processing circuitry including, but is not limited to, a central processing unit (CPU), an arithmetic logic unit (ALU), a digital signal processor, a microcomputer, a field programmable gate array (FPGA), a programmable logic unit, a microprocessor, application-specific integrated circuit (ASIC), etc. The processing circuitry may be special purpose processing circuitry that configures the shoe-type device 1 to set an intensity of a vibration generated by the vibrators to be directly related to a magnitude of pressure measured by the pressure sensors. Therefore, the special purpose controller 24 may improve the functioning of the shoe-type device 1 by controlling a vibration intensity of the vibrators based on a pressure as described above, and thus relieve inconvenience a user may experience due to an excessive vibration.

Figure 4:
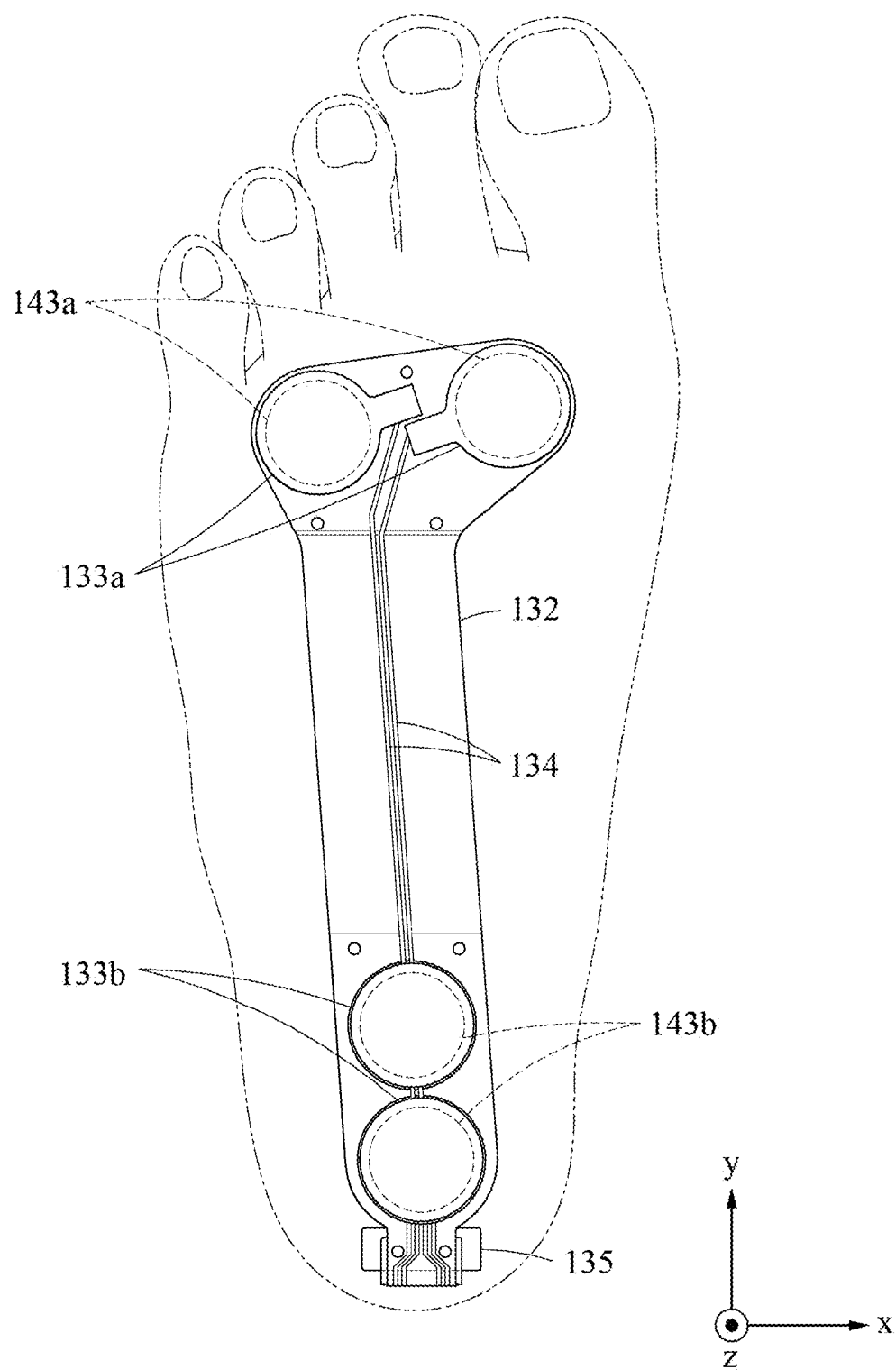
FIG. 4 is a plan view illustrating an example of a positional relationship between electronic devices of a shoe-type device and a foot of a user according to at least one example embodiment.

FIG. 4 is a plan view illustrating an example of a relationship between relative positions of an electronic device and a foot of a user according to at least one example embodiment.

Referring to FIG. 4, a shoe-type device includes a front vibrator 133a disposed in a front portion of the support layer 132, a rear vibrator 133b disposed in a rear portion of the support layer 132, a front pressure sensor 143a disposed under the front vibrator 133a, and a rear pressure sensor 143b disposed under the rear vibrator 133b. The front vibrator 133a may generate a vibration or vibration noise at a position corresponding to a forefoot of a foot of a user, and the rear vibrator 133b may generate a vibration or vibration noise at a position corresponding to a rearfoot of the foot of the user. Here, the forefoot may indicate an anterior sole portion of the foot, and the rearfoot may indicate a posterior sole portion of the foot.

According to an example embodiment, the controller 24 may determine an intensity of a vibration to be generated by the front vibrator 133a based on a pressure measured by the front pressure sensor 143a, and an intensity of a vibration to be generated by the rear vibrator 133b based on a pressure measured by the rear pressure sensor 143b.

An intensity of a vibration or a transfer characteristic of the vibration to be felt by the user may vary according to a change in pressure of a sole of the foot of the user while the user is wearing the shoe-type device 1. For example, when the user is standing with the shoe-type device 1 on, a pressure to be applied to the sole of the foot of the user may be relatively great. In this example, a vibration of a greater intensity may need to be applied to the sole of the foot of the user. For another example, when the user is sitting or lying with the shoe-type device 1 on, a pressure to be applied to the sole of the foot of the user may be relatively smaller than that when the user is standing. In this example, a vibration of a smaller intensity may need to be applied to the sole of the foot of the user. As described above, a pressure on the sole and an intensity of a vibrator to be applied may have a close relationship. Thus, to determine a vibration intensity suitable for each of the vibrators 133a and 133b, a more accurate pressure may need to be measured from a position at which each of the vibrators 133a and 133b is disposed.

The shoe-type device 1 may have the pressure sensors 143a and 143b under the vibrators 133a and 133b, and thus effectively determine an intensity of a vibration corresponding to a position at which a pressure of the sole is measured. In addition, as the pressure sensors 143a and 143b are disposed under the vibrators 133a and 133b, the vibrators 133a and 133b may naturally perform a function corresponding to a puck structure of the pressure sensors 143a and 143b.

FIGS. 5A through 5E are diagrams illustrating examples of an arrangement of a vibrator and a pressure sensor according to at least one example embodiment.

According to an example embodiment, a vibrator and a pressure sensor may form a vertical layer structure, and at least a portion of them may overlap each other in a direction vertical to a bottom surface of a shoe-type device. There may be various forms of the vertical layer structure formed between the vibrator and the pressure sensor. The vibrators 133a, 133b may be one of vibrators 512, 522, 532, 542 and 552, and the pressure sensors 143a, 143b may be a corresponding one of pressure sensors 514, 524, 534, 544 and 554, which are each discussed in more detail below.

Figure 5A:
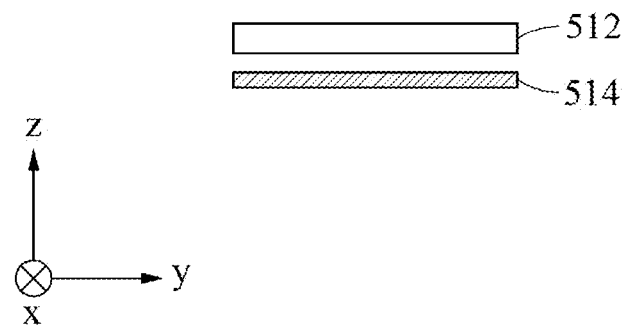
FIGS. 5A through 5E are diagrams illustrating examples of an arrangement relationship between a vibrator and a pressure sensor according to at least one example embodiment.
Figure 5B:
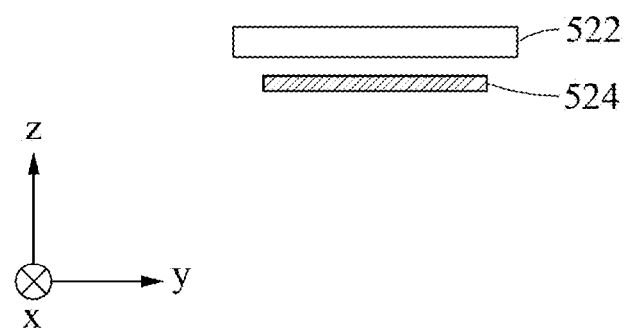
Figure 5C:
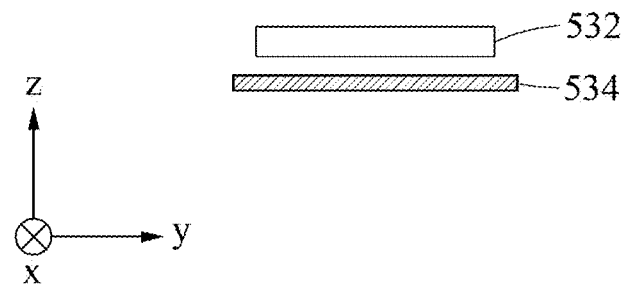
Figure 5D:
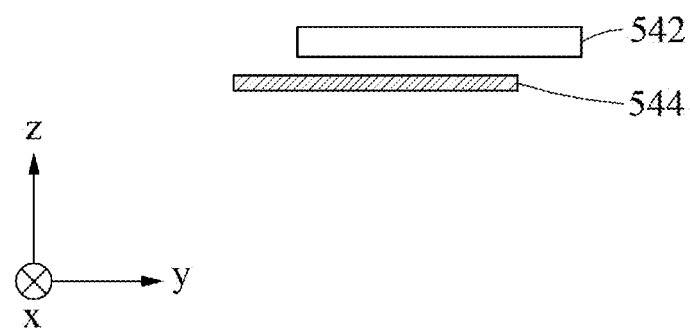
Figure 5E:
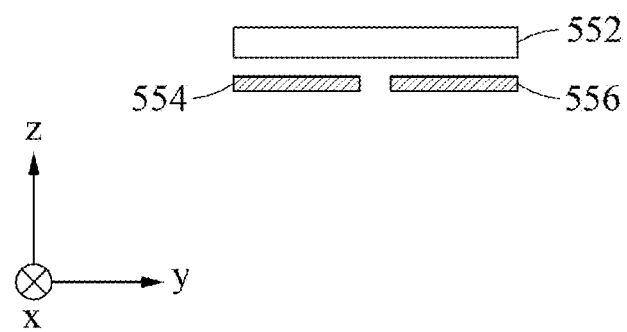

Referring to FIG. 5A, a vibrator 512 and a pressure sensor 514 have a same width, and a same center position in a first direction. For example, the vibrator 512 and the pressure sensor 514 may be arranged within a concentric circle in the first direction. The first direction may correspond to a z-axis direction or a direction vertical to a bottom surface of a shoe-type device. Referring to FIG. 5B, a pressure sensor 524 completely overlaps a vibrator 522 in an area of the vibrator 522 in a direction vertical to a bottom surface of a shoe-type device. In such a case, the vibrator 522 may have a width greater than that of the pressure sensor 524. Referring to FIG. 5C, a vibrator 532 completely overlaps a pressure sensor 534 in an area of the pressure sensor 534 in a direction vertical to a bottom surface of a shoe-type device. In such a case, the pressure sensor 534 may have a width greater than that of the vibrator 532. Referring to FIG. 5D, dissimilar to what is illustrated in FIG. 5A, a vibrator 542 and a pressure sensor 544 may not have a same center position in a first direction. Referring to FIG. 5E, there are a plurality of pressure sensors 554 and 556 associated with a single vibrator 552. In such a case, all the pressure sensors 554 and 556 may be disposed under a vibrator 552, and at least a portion of them may overlap the vibrator 552 in a direction vertical to a bottom surface of a shoe-type device.

According to an example embodiment, a pressure sensor may be attached to a vibrator and may be under the vibrator. In addition, the vibrator and the pressure sensor may be provided in an integral form with the pressure sensor being disposed under the vibrator. That is, the vibrator and the pressure sensor may be embodied by a single module.

Figure 6:
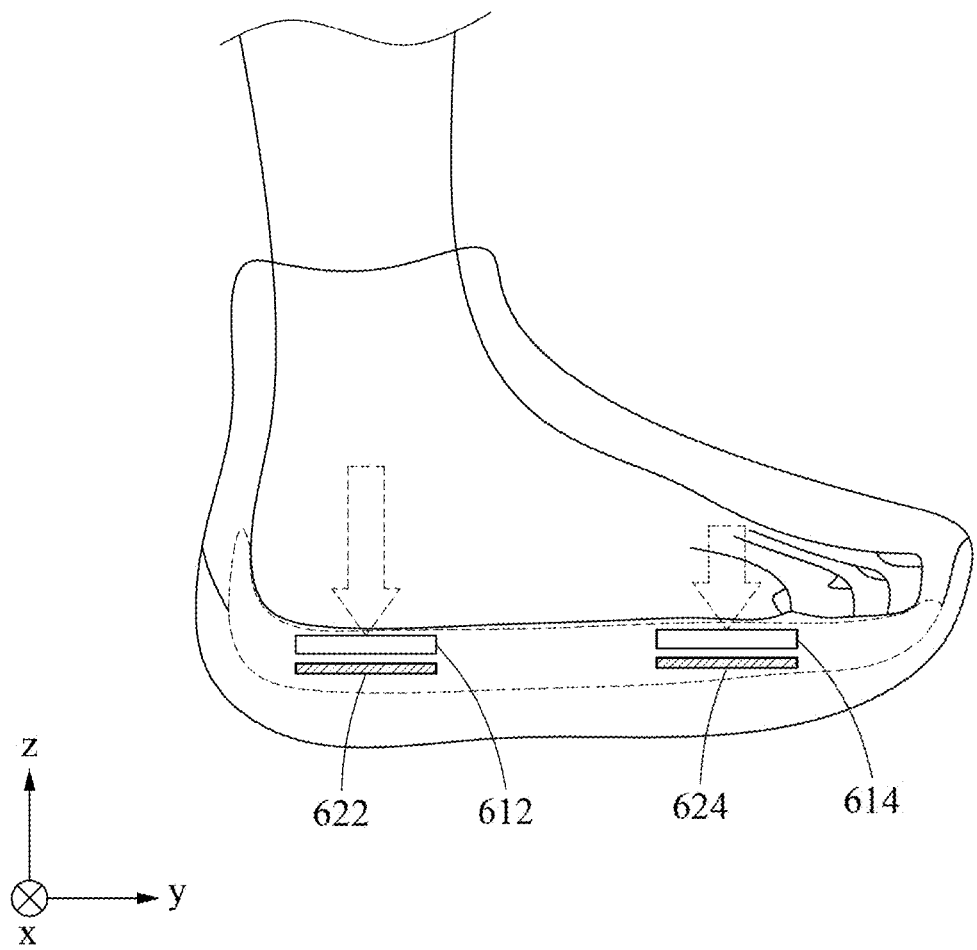
FIG. 6 is a diagram illustrating an example of vibration control of a shoe-type device for a forefoot and a rearfoot of a user according to at least one example embodiment.

FIG. 6 is a diagram illustrating an example of vibration control of a shoe-type device for a forefoot and a rearfoot of a foot of a user according to at least one example embodiment.

Referring to FIG. 6, a shoe-type device includes a front vibrator 614 disposed at a position corresponding to a forefoot of a foot of a user, and a rear vibrator 612 disposed at a position corresponding to a rearfoot of the foot of the user. A front pressure sensor 624 is disposed under the front vibrator 614 and a rear pressure sensor 622 is disposed under the rear vibrator 612. Here, a forefoot and a rearfoot may indicate an anterior sole portion of a foot and a posterior sole portion of the foot, respectively.

When the user is standing on a flat ground with the shoe-type device on, a pressure to be applied to the rearfoot may be generally greater than a pressure to be applied to the forefoot. In such a general case, a pressure to be sensed by the rear pressure sensor 622 may be greater than a pressure to be sensed by the front pressure sensor 624, and thus a controller of the shoe-type device may control the front vibrator 614 and the rear vibrator 612 such that a vibration intensity of the rear vibrator 612 is greater than a vibration intensity of the front vibrator 614. The controller may automatically control the vibration intensity of each of the front vibrator 614 and the rear vibrator 612 based on the pressure sensed by each of the front pressure sensor 624 and the rear pressure sensor 622. Thus, the shoe-type device may effectively trigger stochastic resonance that increases sensitivity of a foot sole of the user based on a pressure on the foot sole of the user.

FIGS. 7A through 7D are diagrams illustrating examples of adjusting a vibration intensity of a vibrator based on a magnitude of a pressure measured by a pressure sensor according to at least one example embodiment.

Figure 7A:
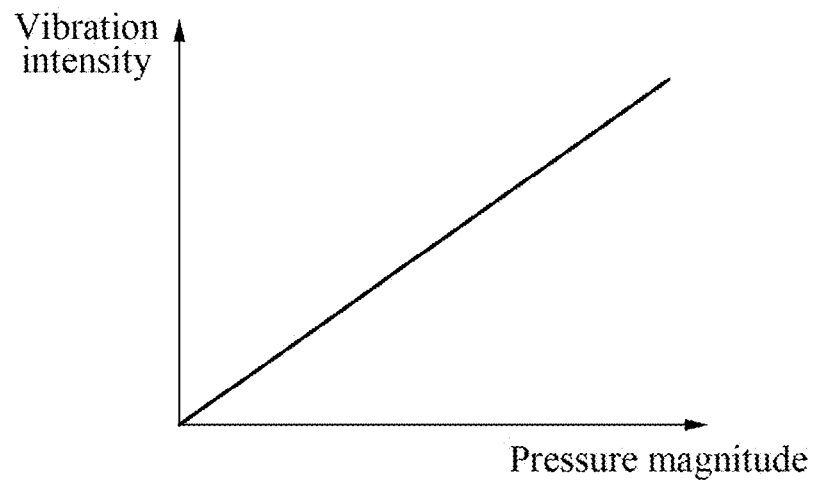
FIGS. 7A through 7D are diagrams illustrating examples of adjusting a vibration intensity of a vibrator based on a magnitude of a pressure measured by a pressure sensor according to at least one example embodiment.
Figure 7B:
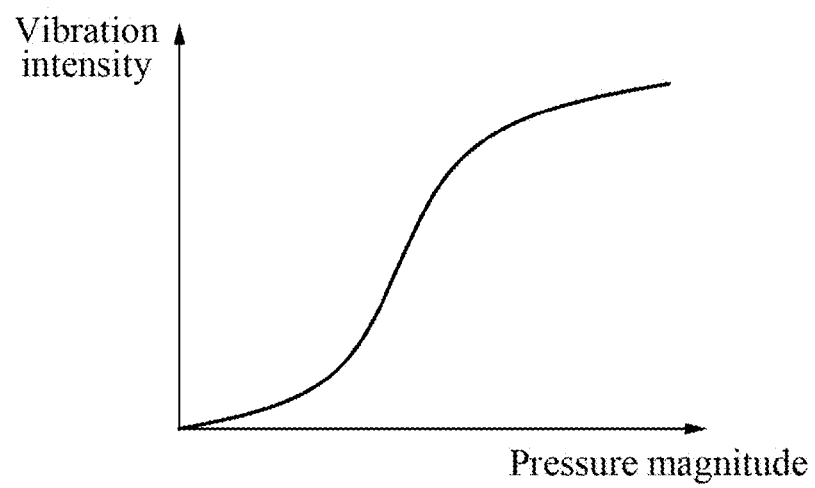
Figure 7C:
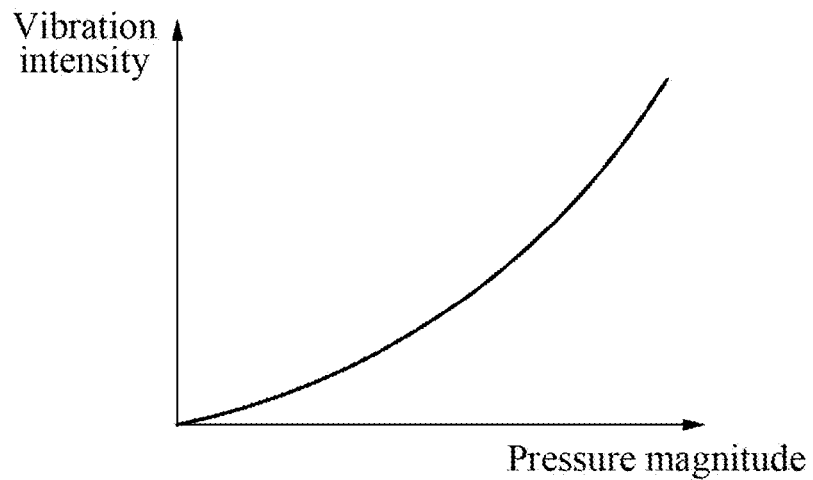
Figure 7D:
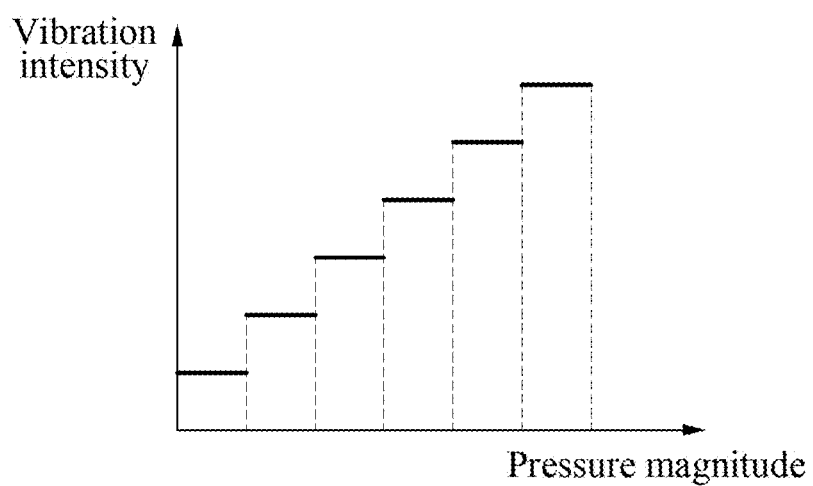

FIG. 7A illustrates an example of linearly adjusting a vibration intensity of a vibrator based on a magnitude of a measured pressure. FIGS. 7B and 7C illustrate examples of non-linearly adjusting a vibration intensity of a vibrator based on a magnitude of a measured pressure. FIG. 7D illustrates non-continuously adjusting a vibration intensity of a vibrator based on a magnitude of a measured pressure.

When a magnitude of a measured pressure is small, a shoe-type device may set an intensity of a vibration to be generated by a vibrator to be small based on, for example, the pressure-intensity relationship illustrated in one of FIGS. 7A to 7D. When a magnitude of a measured pressure is great, the shoe-type device may set an intensity of a vibration to be generated by the vibrator to be great based on, for example, the pressure-intensity relationship illustrated in one of FIGS. 7A to 7D. Thus, the shoe-type device may control a vibration intensity of the vibrator based on a pressure as described above, and thus relieve inconvenience a user may experience due to an excessive vibration.

Figure 8:
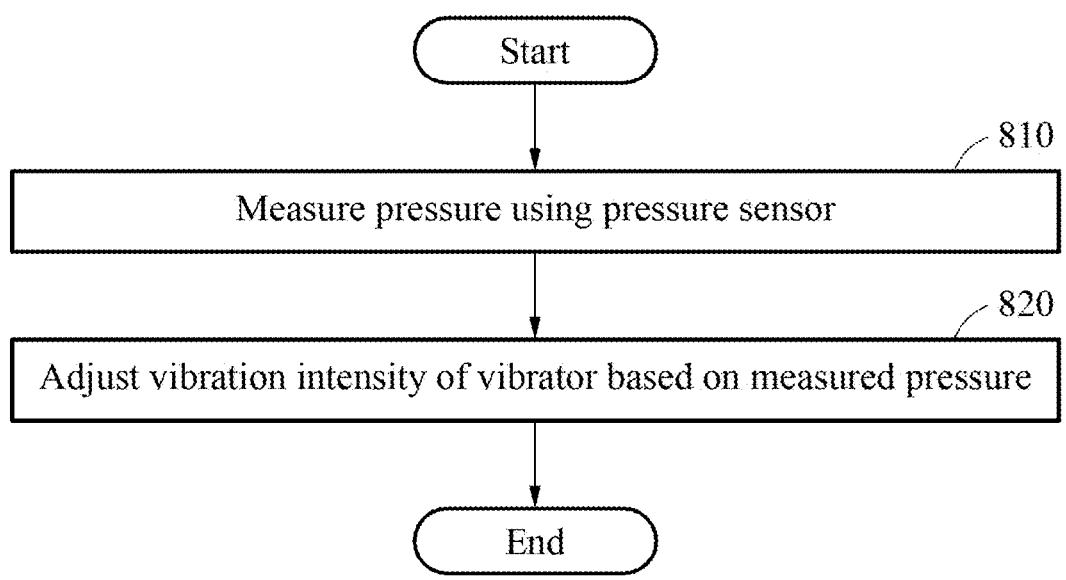
FIG. 8 is a flowchart illustrating an example of a method of controlling a shoe-type device according to at least one example embodiment.

FIG. 8 is a flowchart illustrating an example of a method of controlling a shoe-type device according to at least one example embodiment.

Referring to FIG. 8, in operation 810, the control device 20 of the shoe-type device 1 measures a pressure using the pressure sensors 143*a*, 143*b* disposed under respective ones of the vibrators 133*a*, 133*b*.

In operation 820, the control device 20 of the shoe-type device 1 adjusts an intensity of a vibration to be generated by the vibrators 133*a*, 133*b* based on the pressure measured in operation 810.

According to an example embodiment, when the measured pressure increases, the control device 20 may control the vibrators 133*a*, 133*b* such that an intensity of the vibration to be generated by the vibrators 133*a*, 133*b* increases. Conversely, when the measured pressure decreases, the control device 20 may control the vibrators 133*a*, 133*b* such that an intensity of the vibration to be generated by the vibrator decreases. The control device 20 may adjust a vibration intensity of the vibrator 20 by controlling an output of a motor included in the vibrators 133*a*, 133*b*. The control device 20 may automatically adjust a vibration intensity of the vibrators 133*a*, 133*b* based on a change in measured pressure.

According to an example embodiment, when the shoe-type device 1 includes the first vibrator 133*a* configured to generate a vibration at a position corresponding to a forefoot of a foot of a user, the second vibrator 133*b* configured to generate a vibration at a position corresponding to a rearfoot of the foot of the user, the first pressures sensor 143*a* disposed under the first vibrator 133*a*, and the second pressure sensor 143*b* disposed under the second vibrator 133*b*, the control device 20 may determine an intensity of a first vibration to be generated by the first vibrator 133*a* based on a pressure measured by the first pressure sensor 143*a* and determine an intensity of a second vibration to be generated by the second vibrator 133*b* based on a pressure measured by the second pressure sensor 143*b*. The intensity of the first vibration and the intensity of the second vibration may differ from each other.

A magnitude of a measured foot sole pressure and a vibration intensity of the vibrator to be set based on pressure may have a continuous or non-continuous relationship, or a linear or non-linear relationship for example, as illustrated in FIGS. 7A to 7D. According to an example embodiment, the control device 20 may determine a vibration intensity corresponding to a measured pressure based on desired (or, alternatively, predefined) pressure-vibration intensity conversion information, and control the vibrators 133*a*, 133*b* such that a vibration of the determined vibration intensity is generated.

The shoe-type device 1 may adjust a vibration intensity of the vibrators 133*a*, 133*b* based on a pressure measured from a sole of a foot of the user, and thus reduce a battery consumption of the shoe-type device 1 and effectively trigger stochastic resonance. In addition, when a pressure of the sole of the foot of the user is relatively low, the shoe-type device 1 may apply a vibration of a desirable intensity corresponding to such a low pressure to the sole of the foot of the user, and thus prevent the user from feeling uncomfortableness due to a vibration intensity that is unnecessarily great.

In addition, a vibration frequency of a vibration to be generated by the vibrators 133*a*, 133*b* may be different from a sensing frequency of the pressure sensors 143*a*, 143*b* for pressure sensing, and thus the vibration generated by the vibrators 133*a*, 133*b* may not have a significant influence on the pressure sensing even though the pressure sensor is disposed under the vibrator s 133*a*, 133*b*. According to an example, the control device 20 may use a filter to filter out a noise component that occurs due to a vibration of the vibrators 133*a*, 133*b* from a pressure signal measured by the pressure sensors 143*a*, 143*b*.

In some example embodiments, the shoe-type device 1 may adjust the vibration intensity of the vibrator based on the measured pressure and the pressure-vibration intensity conversion information such that the vibration intensity is within an allowed intensity range.

For example, in some example embodiments, the shoe-type device 1 may set the allowed intensity range based on parameters associated with the user. For example, the shoe-type device 1 may determine a weight of the user based on, for example, the pressure exerted on the pressure sensors 143a, 143b while the user is stationary, and determine the allowed intensity range based on the weight of the user. As another example, the shoe-type device 1 may be configured to perform an initialization operation to determine the sensitivity of the user by providing stimulus to the plantar sole of the user via the vibrators 133a, 133b and receive feedback from the user indicating a minimum acceptable intensity and a maximum acceptable intensity, determine the allowed intensity range based on the input minimum acceptable intensity and maximum acceptable intensity, and store the allowed intensity range in a memory. As another example, the shoe-type device 1 may over time learn over the minimum intensity provided to the user in which the user responds to the stimulus, and store the minimum intensity as the minimum acceptable intensity of the allowed intensity range.

Figure 9:
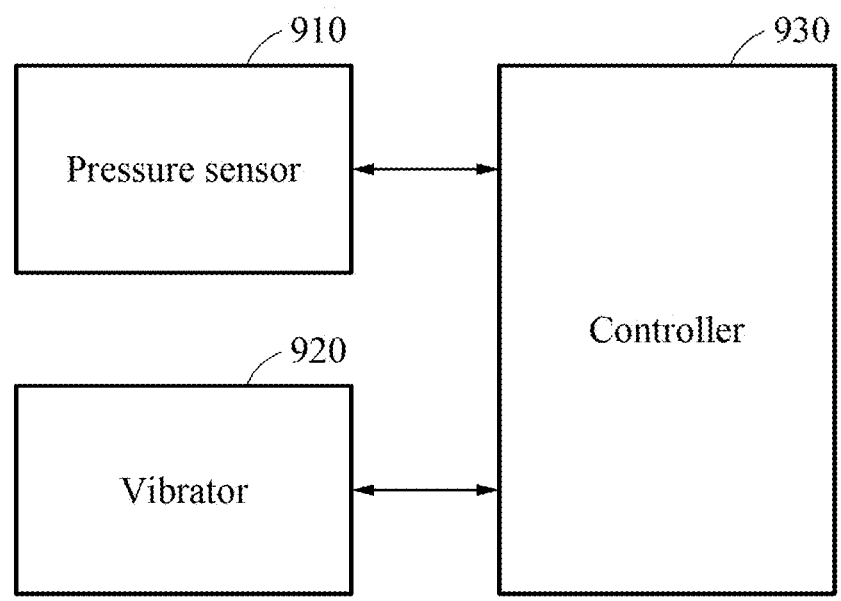
FIG. 9 is a diagram illustrating an example of a control device of a shoe-type device according to at least one example embodiment.

FIG. 9 is a diagram illustrating an example of a control device of a shoe-type device according to at least one example embodiment.

Referring to FIG. 9, a control device 900 of the shoe-type device 1 includes a pressure sensor 910, a vibrator 920, and a controller 930. The control device 900 may be embedded in the shoe-type device 1 to operate therein.

The vibrator 920 may generate a vibration under the control of the controller 930. According to an example embodiment, the vibrator 920 may generate a vibration of an intensity less than a sensory threshold of a user wearing the shoe-type device. The pressure sensor 910 may be disposed under the vibrator 920 and measure a pressure. According to an example embodiment, the vibrator 920 and the pressure sensor 910 may be disposed in an insole of the shoe-type device 1 such that the vibrator 920 corresponds to the vibrators 133a, 133b and the pressure sensor 910 corresponds to the pressure sensors 143a, 143b.

At least a portion of the pressure sensor 910 may overlap the vibrator 920 in a direction vertical to a bottom surface of the shoe-type device 1. According to an example embodiment, the pressure sensor 910 may completely overlap an area of the vibrator 920 in the direction vertical to the bottom surface of the shoe-type device, or the vibrator 920 may completely overlap an area of the pressure sensor 910 in the direction vertical to the bottom surface of the shoe-type device. According to an example, the pressure sensor 910 may be attached to the vibrator 920 under the vibrator 920, and the vibrator 920 and the pressure sensor 910 may be provided in an integral form.

The controller 930 may control each component of the shoe-type device 1. The controller 930 may control an intensity of a vibration to be generated by the vibrator 920 based on a pressure measured by the pressure sensor 910. The controller 930 may correspond to the control device 20.

For example, the controller 930 associated with the shoe-type device 1 may include processing circuitry including, but is not limited to, a central processing unit (CPU), an arithmetic logic unit (ALU), a digital signal processor, a microcomputer, a field programmable gate array (FPGA), a programmable logic unit, a microprocessor, application-specific integrated circuit (ASIC), etc. The processing circuitry may be special purpose processing circuitry that configures the shoe-type device 1 to set an intensity of a vibration generated by the vibrator 920 to be directly related to a magnitude of pressure measured by the pressure sensor 910. Therefore, the special purpose controller 930 may improve the functioning of the shoe-type device 1 by controlling a vibration intensity of the vibrator 920 based on a pressure as described above, and thus relieve inconvenience a user may experience due to an excessive vibration.

For example, when the measured pressure increases, the controller 930 may control the vibrator 920 such that an intensity of the vibration to be generated by the vibrator 920 increases. When the measured pressure decreases, the controller 930 may control the vibrator 920 such that an intensity of the vibration to be generated by the vibrator 920 decreases. For example, when the measured pressure is a first pressure, the controller 930 may set a vibration intensity to be a first intensity. When the measured pressure is a second pressure which is greater than the first pressure, the controller 930 may set a vibration intensity to be a second intensity which is greater than the first intensity.

According to an example embodiment, the controller 930 may use desired (or, alternatively, predefined) pressure-vibration intensity conversion information to determine a vibration intensity of the vibrator 920 based on a magnitude of a measured pressure. The pressure-vibration intensity conversion information may be information that defines a corresponding relationship between a magnitude of a pressure and an intensity of a vibration, and be defined in a form of a lookup table.

The controller 930 may individually control a vibration intensity of each vibrator 920 based on a pressure magnitude of each pressure sensor 910 disposed in the shoe-type device. For example, the controller 930 may determine an intensity of a first vibration to be generated by a first vibrator 920 based on a pressure measured by a first pressure sensor 910, and determine an intensity of a second vibration to be generated by a second vibrator 920 based on a pressure measured by a second pressure sensor 910.

Figure 10:
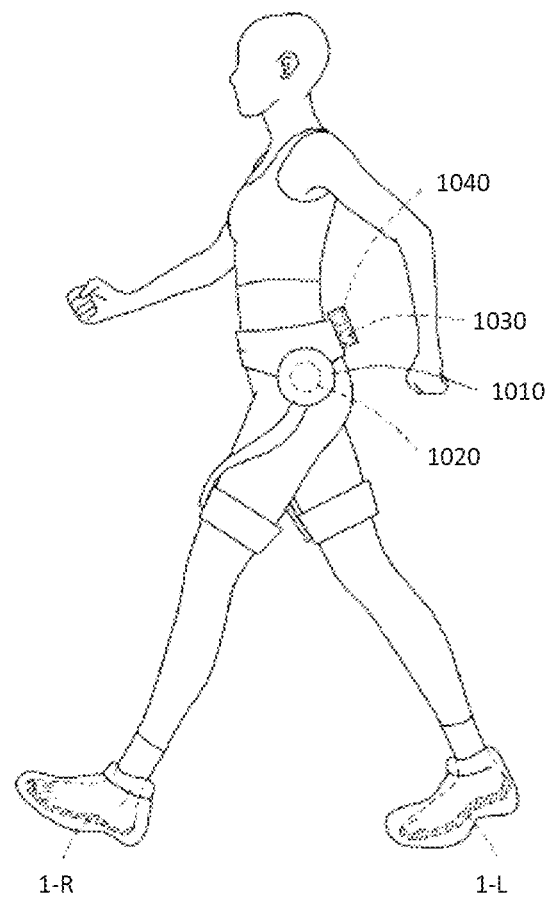
FIG. 10 is a diagram illustrating an example of a walking assistance device according to at least one example embodiment.

FIG. 10 is a diagram illustrating an example of a walking assistance device according to at least one example embodiment.

Referring to FIG. 10, a walking assistance device may be in communication with left and right shoe-type devices 1-L and 1-R, which each correspond to the shoe-type device 1.

In some example embodiments, the walking assistance device may include a driving portion 1010, a sensor portion 1020, an inertial measurement unit (IMU) sensor 1030, and a controller 1040.

In some example embodiments, the shoe-type devices 1-L, 1-R may be in communication with the walking assistance apparatus worn by the user, and may provide information to the walking assistance apparatus indicating the pressure measured by the pressure sensors 143a, 143b and/or may control the vibrators 133a, 133b based on received instructions from the walking assistance apparatus.

In some example embodiments, the shoe-type devices 1-L, 1-R may measure a pressure applied to the sole of the user using the pressure sensors 143a, 143b, and detect a center of pressure (COP) therefrom. The shoe-type device 1 may be in communication with a walking assistance apparatus worn by the user, and instruct the walking assistance apparatus to output an assistance force that re-balances pressures applied to the sole of the user based on the center of pressure (COP).

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A shoe-type device, comprising:
    a first vibrator configured to generate a vibration;
    a first pressure sensor under the vibrator such that the first vibrator is configured to be relatively closer than the first pressure sensor to a sole of a user wearing the shoe-type device, the first pressure sensor being configured to measure a pressure; and
    a controller configured to control an intensity of the vibration generated by the first vibrator based on the pressure,
        wherein, in response to a decrease in the pressure, the controller is configured to control the first vibrator to generate the vibration such that the first vibrator maintains outputting of the vibration during the decrease in the pressure while the intensity of the vibration generated by the first vibrator decreases and is less than a sensory threshold of the user wearing the shoe-type device during the decrease in the pressure.

2. The shoe-type device of claim 1, wherein the first vibrator and the first pressure sensor are integrated within a module such that at least a portion of the first pressure sensor overlaps the first vibrator in a direction vertical to a bottom surface of the shoe-type device.

3. The shoe-type device of claim 1, wherein the first vibrator and the first pressure sensor are integrated within a module such that the first pressure sensor and the first vibrator form a vertical layer structure and have a same center position in a first direction.

4. The shoe-type device of claim 1, wherein the first pressure sensor is attached to an underside of the first vibrator.

5. The shoe-type device of claim 1, wherein the controller is configured to set a vibration frequency of a vibration generated by the first vibrator different from a sensing frequency of the first pressure sensor.

6. The shoe-type device of claim 1, wherein the controller is configured to control the first vibrator such that the intensity of the vibration increases, in response to an increase in the pressure.

7. The shoe-type device of claim 1, wherein the controller is configured to,
    set the intensity of the vibration as a first intensity, in response to the pressure being a first pressure, and
    set the intensity of the vibration as a second intensity greater than the first intensity, in response to the pressure being a second pressure greater than the first pressure.

8. The shoe-type device of claim 1, wherein the controller is configured to determine the intensity of the vibration based on the pressure and pressure-vibration intensity conversion information that defines a corresponding relationship between a magnitude of the pressure and the intensity of the vibration.

9. The shoe-type device of claim 1, wherein the first vibrator is configured to generate the vibration at a position corresponding to a forefoot of a foot of the user, and the shoe-type device further comprises:
    a module including a second vibrator and a second pressure sensor integrated therein such that the second pressure sensor is located under the second vibrator within the module, the second vibrator configured to generate another vibration at a position corresponding to a rearfoot of the foot of the user.

10. The shoe-type device of claim 9, wherein the controller is configured to,
  determine an intensity of the vibration to be generated by the first vibrator based on the pressure measured by the first pressure sensor, and
  determine an intensity of the another vibration to be generated by the second vibrator based on another pressure measured by the second pressure sensor.

11. The shoe-type device of claim 10, wherein the controller is configured to control the first vibrator and the second vibrator such that the intensity of the vibration and the intensity of the another vibration differ from each other.

12. The shoe-type device of claim 2, wherein the first vibrator and the first pressure sensor are integrally formed within the module such that the module is removable from the shoe-type device while the first vibrator and the first pressure sensor remain overlapping each other within the module.

13. The shoe-type device of claim 1, wherein the first pressure sensor is configured to measure a first pressure at a position corresponding to a forefoot of a foot of the user, and the shoe-type device further comprises:
  a second vibrator configured to generate another vibration at a position corresponding to a rearfoot of the foot of the user; and
  a second pressure sensor under the second vibrator, the second pressure sensor being configured to measure a second pressure the position corresponding to the rearfoot of the foot of the user, wherein
    the controller is configured to control the first vibrator and the second vibrator based on the first pressure and the second pressure such that an intensity of the vibration generated by the first vibrator and an intensity of the vibration generated by the second vibrator differ from each other based on a difference between the first pressure and the second pressure.

14. A method of controlling a shoe-type device, the shoe-type device including a first vibrator, a first pressure sensor under the first vibrator such that the first vibrator is configured to be relatively closer than the first pressure sensor to a sole of user wearing the shoe-type device, and a controller, the method comprising:
  measuring, via the first pressure sensor, a pressure; and
  controlling, by the controller, an intensity of a vibration generated by the first vibrator based on the pressure,
    wherein, in response to a decrease in the pressure, the controlling comprises controlling the first vibrator to generate the vibration such that the first vibrator maintains outputting of the vibration during the decrease in the pressure while the intensity of the vibration generated by the first vibrator decreases and is less than a sensory threshold of the user wearing the shoe-type device during the decrease in the pressure.

15. The method of claim 14, wherein the first vibrator and the first pressure sensor are integrated within a module such that, within the module, at least a portion of the first pressure sensor overlaps the first vibrator in a direction vertical to a bottom surface of the shoe-type device.

16. The method of claim 14, wherein the controlling comprises:
  controlling the first vibrator such that the intensity of the vibration increases, in response to an increase in the pressure.

17. The method of claim 14, wherein the first vibrator is configured to generate the vibration at a position corresponding to a forefoot of a foot of the user, and the shoe-type device further includes a module including a second vibrator and a second pressure sensor integrated therein such that the second pressure sensor is located under the second vibrator within the module, the second vibrator configured to generate another vibration at a position corresponding to a rearfoot of the foot of the user, and wherein the controlling comprises:
  determining an intensity of the vibration to be generated by the first vibrator based on the pressure measured by the first pressure sensor; and
  determining an intensity of the another vibration to be generated by the second vibrator based on another pressure measured by the second pressure sensor.

18. The method of claim 15, wherein the first vibrator and the first pressure sensor are integrally formed within the module such that the module is removable from the shoe-type device while the first vibrator and the first pressure sensor remain overlapping each other within the module.

19. The method of claim 14, wherein the first pressure sensor is configured to measure a first pressure at a position corresponding to a forefoot of a foot of the user, and the shoe-type device further includes a second vibrator configured to generate another vibration at a position corresponding to a rearfoot of the foot of the user and a second pressure sensor under the second vibrator, the second pressure sensor being configured to measure a second pressure the position corresponding to the rearfoot of the foot of the user, wherein the controlling comprises:
  controlling, by the controller, the first vibrator and the second vibrator based on the first pressure and the second pressure such that an intensity of the vibration generated by the first vibrator and an intensity of the vibration generated by the second vibrator differ from each other based on a difference between the first pressure and the second pressure.

20. An insole of a shoe-type device, the insole comprising:
  an insole body insertable in the shoe-type device;
  a first vibrator installed in the insole body, the first vibrator configured to generate a vibration; and
  a first pressure sensor under the first vibrator in the insole body such that the first vibrator is configured to be relatively closer than the first pressure sensor to a sole of user wearing the shoe-type device, the first pressure sensor being configured to measure a pressure,
    wherein, in response to a decrease in the pressure, the first vibrator generates the vibration such that the first vibrator maintains outputting of the vibration during the decrease in pressure while an intensity of the vibration generated by the first vibrator decreases and is less than a sensory threshold of the user wearing the shoe-type device during the decrease in the pressure.

21. The insole of claim 20, wherein the first vibrator and the first pressure sensor are integrated within a module such that at least a portion of the first pressure sensor overlaps the first vibrator in a direction vertical to a bottom surface of the insole.

22. The insole of claim 20, wherein the first vibrator is configured to generate the vibration at a position corresponding to a forefoot of a foot of the user, and the insole further comprises:
  a module including a second vibrator and a second pressure sensor integrated therein such that the second pressure sensor is located under the second vibrator within the module, the second vibrator configured to generate another vibration at a position corresponding to a rearfoot of the foot of the user.

23. The insole of claim 20, wherein the intensity of the vibration is based on the pressure such that the intensity of the vibration varies directly with the pressure.

24. The insole of claim 20, further comprising:
a connector configured to connect the first vibrator and the first pressure sensor to a controller.

25. The insole of claim 24, wherein the connector is configured to at least partially protrude from the insole body downwards towards an outsole of the shoe-type device to contact a terminal of the controller.

26. The insole of claim 24, further comprising:
the controller connected to the first vibrator and the first pressure sensor via the connector, the controller configured to control an intensity of the vibration generated by the first vibrator based on the pressure; and
a module including the first vibrator and the first pressure sensor integrated therein such that the first pressure sensor is located under the first vibrator within the module.

27. The insole of claim 21, wherein the first vibrator and the first pressure sensor are integrally formed within the module such that the module is removable from the shoe-type device while the first vibrator and the first pressure sensor remain overlapping each other within the module.

28. The insole of claim 20, wherein the first pressure sensor is configured to measure a first pressure at a position corresponding to a forefoot of a foot of the user, and the shoe-type device further comprises:
a second vibrator configured to generate another vibration at a position corresponding to a rearfoot of the foot of the user; and
a second pressure sensor under the second vibrator, the second pressure sensor being configured to measure a second pressure the position corresponding to the rearfoot of the foot of the user, wherein
based on the first pressure and the second pressure, an intensity of the vibration generated by the first vibrator and an intensity of the vibration generated by the second vibrator differ from each other based on a difference between the first pressure and the second pressure.

\* \* \* \* \*